(12) United States Patent
Morris et al.

(10) Patent No.: US 7,198,783 B2
(45) Date of Patent: Apr. 3, 2007

(54) SENSITIZATION OF NEOPLASTIC CELLS TO RADIATION THERAPY WITH REOVIRUS

(75) Inventors: Donald Morris, Calgary (CA); Matthew C. Coffey, Calgary (CA); Bradley G. Thompson, Calgary (CA); Douglas Ball, Calgary (CA)

(73) Assignee: Oncolytics Biotech Inc., Calgary, Alberta (CA)

( * ) Notice: Subject to any disclaimer, the term of this patent is extended or adjusted under 35 U.S.C. 154(b) by 216 days.

(21) Appl. No.: 10/431,579

(22) Filed: May 8, 2003

(65) Prior Publication Data
US 2004/0091463 A1 May 13, 2004

Related U.S. Application Data

(60) Provisional application No. 60/443,189, filed on Jan. 29, 2003, provisional application No. 60/378,948, filed on May 10, 2002.

(51) Int. Cl.
A01N 63/00 (2006.01)
A61K 39/15 (2006.01)
C12N 15/00 (2006.01)

(52) U.S. Cl. .................. 424/93.1; 424/93.2; 424/215.1
(58) Field of Classification Search ............... 424/93.2, 424/93.1, 9.1, 1.11, 1.65, 215.1; 435/320.1
See application file for complete search history.

(56) References Cited

U.S. PATENT DOCUMENTS

| 6,100,243 | A | 8/2000 | Frisch |
| 6,136,307 | A | 10/2000 | Lee et al. |
| 6,565,831 | B1 * | 5/2003 | Coffey et al. ............... 424/1.33 |
| 2002/0037576 | A1 | 3/2002 | Thompson et al. |

FOREIGN PATENT DOCUMENTS

| WO | WO 96/07322 A | 3/1996 |
| WO | WO 00/50051 | 8/2000 |
| WO | WO 02/11742 A | 2/2002 |
| WO | WO 02/066040 A | 8/2002 |

OTHER PUBLICATIONS

Bradley et al. Clinical. Cancer Research 1999, vol. 5, pp. 1517-1522.*
Smith et al. Expert Opinion on Investigational Drug 2000, vol. 9, No. 2, pp. 311-327.*
Bar-Eli, N., et al., "preferential cytotoxic effect of Newcastle disease virus on lymphoma cells", J. Cancer Res. Clin. Oncol. 122: 409-415 (1996).
Chandran and Nibert, "Protease cleavage of reovirus capsid protein mu1 and mu1C is blocked by alkyl sulfate detergents, yielding a new type of infectious subvirion particle", J. of Virology 72(1):467-75 (1998).
Chang et al., PNAS 89:4825-4829 (1992).
Chang, H.W. et al., Virology 194:537-547 (1993).
Chang et al., J. Virol. 69:6605-6608 (1995).
Chmura et al., "Strategies for enhancing viral-based gene therapy using ionizing radiation", Radiation oncology Investigations 7:261-269 (1999).
Chmura et al., "Prospects for viral-based strategies enhancing the anti-tumor effects of ionizing radiation", Seminars in Radiation Oncology 11(4):338-345 (2001).
Cuff et al., "Enteric reovirus infection as a probe to study immunotoxicity of the gastrointestinal tract", Toxicological Sciences 42(2):99-108 (1998).
Duncan et al., "Conformational and functional analysis of the C-terminal globular head of the reovirus cell attachment protein", Virology 182(2):810-9 (1991).
Fueyo, J., et al., "A Mutant Oncolytic Adenovirus Targeting the Rb Pathway Produces Anti-Glioma Effect in Vivo", Oncogene 19(1):2-12 (2000).
Kawagishi-Kobayashi, M., et al., Mol. Cell. Biology 17:4146-4158 (1997).
Mah et al., "The N-terminal quarter of reovirus cell attachment protein sigma 1 possesses intrinsic virion-anchoring function", Virology 179(1):95-103 (1990).
Nemunaitis, J., Invest. New Drugs 17:375-386 (1999).
Nibert, M.L., Schiff, L.A., and Fields, B.N., "Reoviruses and their replication", pp. 1557-1596 in Fundamental Virology (Fields et al., 3rd Edition), Lippencott-Raven Press, 1996.
Reichard, K.W., et al., "Newcastle Disease Virus Selectively Kills Human Tumor Cells", J. of Surgical Research 52:448-453 (1992).
Romano et al., Mol. and Cell. Bio. 18:7304-7316 (1998).
Sharp et al., Virol. 250:301-315 (1998).
Turner and Duncan, "Site directed mutagenesis of the C-terminal portion of reovirus protein sigmal: evidence for a conformation-dependent receptor binding domain", Virology 186(1):219-27 (1992).
Yoon, S.S., et al., "An Oncolytic Herpes Simplex Virus Type I Selectively Destroys Diffuse Liver Metastases from Colon Carcinoma", FASEB J.. 14:301-311(2000).
Zorn, U. et al., "Induction of Cytokines and Cytotoxicity against Tumor Cells by Newcastle Disease Virus", Cancer Biotherapy 9(3):22-235 (1994).
Abstract, Oncogene, Oct. 18, 2001;20(47):6910-9, "Caspase 8-dependent sensitization of cancer cells to TRAIL-induced apoptosis following reovirus-infection".

* cited by examiner

Primary Examiner—Bruce R. Campell
Assistant Examiner—Bao Qun Li
(74) Attorney, Agent, or Firm—Fish & Richardson P.C.

(57) ABSTRACT

The present invention relates to methods of sensitizing neoplastic cells to irradiation by using oncolytic viruses, particularly reoviruses. Also provided are methods of treating or ameliorating a tumor with a combination of oncolytic viruses and radiotherapy.

25 Claims, No Drawings

SENSITIZATION OF NEOPLASTIC CELLS TO RADIATION THERAPY WITH REOVIRUS

RELATED APPLICATIONS

This application claims the benefit of U.S. Provisional Applications Ser. No. 60/378,948, filed May 10, 2002; and Ser. No. 60/443,189, filed Jan. 29, 2003. The entire disclosure of these prior applications is hereby incorporated by reference.

FIELD OF THE INVENTION

The present invention relates to methods of sensitizing neoplastic cells to irradiation by using oncolytic viruses, particularly reovirus.

REFERENCES

U.S. Pat. No. 6,136,307.
U.S. Pat. No. 6,100,243.
U.S. Patent Application Publication No. 20020037576.
Bar-Eli, N., et al., "preferential cytotoxic effect of Newcastle disease virus on lymphoma cells", *J. Cancer Res. Clin. Oncol.* 122: 409–415 (1996).
Chandran and Nibert, "Protease cleavage of reovirus capsid protein mu1 and mu1C is blocked by alkyl sulfate detergents, yielding a new type of infectious subvirion particle", J. of Virology 72(1):467–75 (1998).
Chang et al., *PNAS* 89:4825–4829 (1992).
Chang, H. W. et al., *Virology* 194:537–547 (1993).
Chang et al., *J. Virol.* 69:6605–6608 (1995).
Chmura et al., "Strategies for enhancing viral-based gene therapy using ionizing radiation", Radiation oncology Investigations 7:261–269 (1999).
Chmura et al., "Prospects for viral-based strategies enhancing the anti-tumor effects of ionizing radiation", Seminars in Radiation Oncology 11(4):338–345 (2001).
Cuff et al., "Enteric reovirus infection as a probe to study immunotoxicity of the gastrointestinal tract", *Toxicological Sciences* 42(2):99–108 (1998).
Duncan et al., "Conformational and functional analysis of the C-terminal globular head of the reovirus cell attachment protein", Virology 182(2):810–9 (1991).
Fields, B. N. et al., *Fundamental Virology*, 3rd Edition, Lippincott-Raven (1996).
Fueyo, J., et al., "A Mutant Oncolytic Adenovirus Targeting the Rb Pathway Produces Anti-Glioma Effect in Vivo", *Oncogene* 19(1):2–12 (2000).
Harlow et al., "Antibodies. A Laboratory Manual", Cold Spring Harbor Laboratory, New York, 1988.
Kawagishi-Kobayashi, M., et al., *Mol. Cell. Biology* 17:4146–4158 (1997).
Mah et al., "The N-terminal quarter of reovirus cell attachment protein sigma 1 possesses intrinsic virion-anchoring function", Virology 179(1):95–103 (1990).
Nemunaitis, J., *Invest. New Drugs* 17:375–386 (1999).
Nibert, M. L., Schiff, L. A., and Fields, B. N., "Reoviruses and their replication", pages 1557–96 in *Fundamental Virology (Fields et al.,* 3rd Edition), Lippencott-Raven Press, 1996.
Reichard, K. W., et al., "Newcastle Disease Virus Selectively Kills Human Tumor Cells", *J. of Surgical Research* 52:448–453 (1992).
Romano et al., *Mol. and Cell. Bio.* 18:7304–7316 (1998).
Sharp et al., *Virol.* 250:301–315 (1998).
Turner and Duncan, "Site directed mutagenesis of the C-terminal portion of reovirus protein sigma1: evidence for a conformation-dependent receptor binding domain", Virology 186(1):219–27 (1992).
Yoon, S. S., et al., "An Oncolytic Herpes Simplex Virus Type I Selectively Destroys Diffuse Liver Metastases from Colon Carcinoma", FASEB J. 14:301–311(2000).
Zorn, U. et al., "Induction of Cytokines and Cytotoxicity against Tumor Cells by Newcastle Disease Virus", *Cancer Biotherapy* 9(3):22–235 (1994).

All of the publications, patents and patent applications cited above or elsewhere in this application are herein incorporated by reference in their entirety to the same extent as if the disclosure of each individual publication, patent application or patent was specifically and individually indicated to be incorporated by reference in its entirety.

BACKGROUND OF THE INVENTION

Radiotherapy, also called radiation therapy, is the treatment of cancer and other diseases with radiation, typically ionizing radiation. Radiotherapy may be used to treat localized solid tumors, such as cancers of the skin, tongue, larynx, brain, breast, or uterine cervix. It can also be used to treat leukemia and lymphoma.

One type of radiation therapy commonly used involves photons (electromagnetic energy). X-rays were the first form of photon radiation to be used to treat cancer. Depending on the amount of energy they possess, the rays can be used to destroy cancer cells on the surface of or deeper in the body. Linear accelerators and betatrons are machines that produce x-rays of increasingly greater energy. The use of machines to focus radiation (such as x-rays) on a cancer site is called external beam radiotherapy.

Gamma rays are another form of photons used in radiotherapy. Gamma rays are produced spontaneously as certain elements (such as radium, uranium, and cobalt 60) release radiation as they decay. Each element decays at a specific rate and gives off energy in the form of gamma rays and other particles. X-rays and gamma rays have the same effect on cancer cells.

Another technique for delivering radiation to cancer cells is to place radioactive implants directly in a tumor or body cavity. This is called internal radiotherapy, and brachytherapy, interstitial irradiation, and intracavitary irradiation are types of internal radiotherapy. In this treatment, the radiation dose is concentrated in a small area. Internal radiotherapy is frequently used for cancers of the tongue, uterus, and cervix.

Several new approaches to radiation therapy are being evaluated to determine their effectiveness in treating cancer. One such technique is intraoperative irradiation, in which a large dose of external radiation is directed at the tumor and surrounding tissue during surgery. Another investigational approach is particle beam radiation therapy. This type of therapy differs from photon radiotherapy in that it involves the use of fast-moving subatomic particles to treat localized cancers. A very sophisticated machine is needed to produce and accelerate the particles required for this procedure. Some particles (neutrons, pions, and heavy ions) deposit more energy along the path they take through tissue than do x-rays or gamma rays, thus causing damage to the cells they hit. This type of radiation is often referred to as high linear energy transfer (high LET) radiation. Another recent radiotherapy research has focused on the use of radiolabeled antibodies to deliver doses of radiation directly to the cancer site (radioimmunotherapy).

Methods of increasing the effectiveness of radiation therapy have been actively searched. Two types of investigational drugs are being studied for their effects on cells undergoing radiation. Radiosensitizers make the tumor cells more likely to be damaged, and radioprotectors protect normal tissues from the effects of radiation. Hyperthermia, the use of heat, is also being studied for its effectiveness in sensitizing tissue to radiation.

Ideally, a radiosensitizer exerts its function only on the target cells. For the ease of use, the radiosensitizer should also be able to find the target cells even if it is administered systemically. However, the current radiosensitizers are typically not selective for tumor cells, and they are distributed in an animal only by diffusion. Therefore, the need exists for a better radiosensitizer.

SUMMARY OF THE INVENTION

The present invention relates to, inter alia, the unexpected discovery that reovirus can increase the sensitivity of tumor cells to radiation. Reovirus is a highly selective anti-tumor agent, which replicates in and kill ras-activated neoplastic cells only. In the present invention, we demonstrate that tumors may be effectively reduced upon irradiation in conjunction with reovirus treatment. Furthermore, the reovirus needs not be administered to the irradiated tumor directly. Therefore, reovirus is not only a selective radiosensitizer, but it also has a "remote effect", thereby eliminating the necessity of administering the reovirus to each and every tumor mass.

Accordingly, one aspect of the present invention provides a method of sensitizing a neoplastic cell to irradiation, comprising:
(a) administering to said neoplastic cell an effective amount of a reovirus; and
(b) subjecting said cell to an effective dose of an irradiating agent, whereby the sensitivity of the neoplastic cell to the irradiating agent is increased by the reovirus.

The reovirus is preferably administered prior to or concurrently with the irradiation. The reovirus may be any reovirus, preferably a mammalian or avian reovirus. The mammalian reovirus is preferably a human reovirus, more preferably a serotype 3 reovirus, and most preferably the Dearing strain serotype 3 reovirus.

The irradiating agent can be any irradiating agent known in the art, including but not limited to X-rays, gamma rays (e.g., gamma rays produced by radium, uranium, or cobalt 60), and particle beam (e.g., electrons, neutrons, pions, and heavy ions). The irradiation may be in the form of external radiotherapy or internal radiotherapy (including brachytherapy, interstitial irradiation, and intracavitary irradiation). The irradiating agents may be linked to an antibody, as in radioimmunotherapy, or employed during a surgery, as in intraoperative radiotherapy.

The neoplastic cell is preferably located in a mammal, particularly a mammal selected from the group consisting of dogs, cats, rodents, sheep, goats, cattle, horses, pigs, human and non-human primates. Most preferably, the mammal is human.

The reovirus useful in the present invention may be a recombinant reovirus. The recombinant reovirus may be generated by co-infection of mammalian cells with different subtypes of reovirus. The recombinant reovirus may be naturally-occurring or non-naturally-occurring. The recombinant reovirus may be from two or more strains of reovirus, particularly two or more strains of reovirus selected from the group consisting of strain Dearing, strain Abney, strain Jones, and strain Lang. The recombinant reovirus may also result from reassortment of reoviruses from different serotypes, such as selected from the group consisting of serotype 1 reovirus, serotype 2 reovirus and serotype 3 reovirus. The recombinant reovirus may comprise naturally-occurring variant coat protein coding sequences or mutated coat protein coding sequences.

Another aspect of the present invention provides a method of treating or ameliorating a tumor in a subject, comprising:
(a) administering to the subject an effective amount of reovirus under conditions that result in infection of cells of the tumor by the reovirus; and
(b) irradiating the subject with an effective dose of an irradiating agent.

In particular, the tumor is resistant to radiation in the absence of the reovirus.

The reovirus is preferably administered prior to or concurrent with the irradiating agent, particularly prior to the irradiating agent. Both the reovirus and irradiating agent may be administered to the subject in single dose or multiple doses. The subject is preferably a mammal, more preferably a mammal selected from the group consisting of dogs, cats, rodents, sheep, goats, cattle, horses, pigs, human and non-human primates. Most preferably, the subject is human.

Any tumor can be subjected to the claimed method, including solid tumors and hematopoietic tumors. The solid tumor is preferably selected from the group consisting of lung cancer, prostate cancer, colorectal cancer, thyroid cancer, renal cancer, adrenal cancer, liver cancer, pancreatic cancer, breast cancer and central and peripheral nervous system cancer. The hematopoietic tumor is preferably selected from the group consisting of lymphomas and leukemias. The tumor may be a metastatic tumor.

The reovirus may be administered in any manner that ultimately results in contact of reovirus with the target tumor. For example, the reovirus may be administered systemically or locally (e.g., into or near a solid tumor).

Another aspect of the present invention provides a method of preventing a tumor from developing resistance to radiation in a subject, comprising administering an effective amount of a reovirus to said subject.

Yet another aspect of the present invention provides a method of increasing the efficacy of reovirus therapy in an animal having a tumor by exposing the animal to an effective amount of an irradiating agent. The reovirus and the irradiating agent may be administered separately, namely at different times and/or to different sites. For example, the virus may be administered systemically and the irradiating agent to a local tumor. As a result, the irradiated tumor, as well as other tumors in the same animal, reduces in size or slows down its growth to a higher extent than if the virus or irradiating agent is used alone. Similarly, the virus may be administered to a local tumor while another local tumor is irradiated, and all tumors in the same animal are treated or alleviated. The combined effect of the virus and radiation is typically more than an additive effect.

In addition to reovirus, other oncolytic viruses can be used to practice the present invention in the same manner as reovirus. Exemplary oncolytic viruses include, but are not limited to, viruses that have mutations or deletions so as not to inhibit the double stranded RNA activated protein kinase (PKR), Delta24, vesicular stomatitis virus (VSV), Newcastle disease virus (NDV), vaccinia virus, encephalitis virus, herpes zoster virus, hepatitis virus, influenza virus, varicella virus, and measles virus. Preferably, the oncolytic virus (a) is not a viral vehicle for delivering a gene; (b) does not express the adenoviral E1A gene; and/or (c) is not a herpes virus.

In particular, the oncolytic virus and radiation may be administered to different sites in the subject to be treated. Thus, an aspect of the present invention provides a method for sensitizing a neoplastic cell in an animal to irradiation, comprising:
(a) administering to said animal an effective amount of an oncolytic virus; and
(b) subjecting said cell to an effective dose of an irradiating agent, whereby the sensitivity of the neoplastic cell to the irradiating agent is increased by the oncolytic virus, and wherein the oncolytic virus and the irradiating agent are administered to different sites in the animal.

The oncolytic virus may be administered by any route, including systemic administration.

Optionally, the animal may be immune suppressed to avoid immune responses against the therapeutically administered virus. The immune suppression may be specific or non-specific. Thus, the methods of the present invention may be coupled with at least one of the following:
i) administering to the animal an effective amount of an immune suppressive agent;
ii) removing B-cells or T-cells from the animal;
iii) removing anti-virus antibodies from the animal;
iv) removing antibodies from the animal;
v) administering anti-antivirus antibodies to the animal; and
vi) suppressing the immune system of the animal.

DETAILED DESCRIPTION OF THE INVENTION

The present invention relates to, inter alia, the unexpected discovery that reovirus can increase the sensitivity of tumor cells to radiation. Reovirus is a highly selective anti-tumor agent, which replicates in and kills ras-activated neoplastic cells only. In the present invention, we demonstrate that tumors may be effectively reduced upon irradiation in conjunction with reovirus treatment. Furthermore, the reovirus needs not be administered to the irradiated tumor directly. Therefore, reovirus is not only a selective radiosensitizer, but it also has a "remote effect", thereby eliminating the necessity of administering the reovirus to each and every tumor mass. Other oncolytic viruses can be used as well.

Prior to describing the invention in further detail, the terms used in this application are defined as follows unless otherwise indicated.

Definitions

"Sensitizing" a neoplastic cell to radiation, as used herein, refers to the act of enhancing the sensitivity of a neoplastic cell to radiation.

"Sensitivity" of a neoplastic cell to radiation is the susceptibility of the neoplastic cell to the inhibitory effect of radiation. For example, sensitivity of a neoplastic cell to radiation may be indicated by reduction in growth rate of the cell in response to radiation. The sensitivity may also be demonstrated by a reduction of the symptoms caused by the neoplastic cells.

A neoplastic cell that is "resistant" to radiation is a neoplastic cell not killed or growth inhibited by radiation. To determine if a neoplastic cell is growth inhibited, the growth rate of the cell in the presence or absence of radiation can be determined by established methods in the art, such as cell counts. The neoplastic cell is not growth inhibited by radiation if the growth rate is not significantly different with or without radiation.

A tumor that is "resistant" to radiation is a tumor of which the rate of size increase or weight increase does not change in the presence of radiation. Alternatively, if the subject bearing the tumor displays similar symptoms or indicators of the tumor whether the subject receives radiation or not, the tumor is resistant to radiation. For example, white cell count is commonly used as an indicator of leukemia. If the white cell count of a leukemia patient does not significantly change after receiving radiation, the leukemia of this patient is resistant to radiation.

A "neoplastic cell", "tumor cell", or "cell with a proliferative disorder", refers to a cell which proliferates at an abnormally high rate. A new growth comprising neoplastic cells is a neoplasm, also known as a "tumor". A tumor is an abnormal tissue growth, generally forming a distinct mass, that grows by cellular proliferation more rapidly than normal tissue growth. A tumor may show partial or total lack of structural organization and functional coordination with normal tissue. As used herein, a tumor is intended to encompass hematopoietic tumors as well as solid tumors.

A tumor may be benign (benign tumor) or malignant (malignant tumor or cancer). Malignant tumors can be broadly classified into three major types. Malignant tumors arising from epithelial structures are called carcinomas, malignant tumors that originate from connective tissues such as muscle, cartilage, fat or bone are called sarcomas and malignant tumors affecting hematopoietic structures (structures pertaining to the formation of blood cells) including components of the immune system, are called leukemias and lymphomas. Other tumors include, but are not limited to neurofibromatosis.

A "lesion" is an injury, wound or an area that is structurally abnormal. In the context of a subject bearing tumor, a lesion is a tumor mass unless otherwise described.

"Ras-activated neoplastic cells" or "ras-mediated neoplastic cells" refer to cells which proliferate at an abnormally high rate due to, at least in part, activation of the ras pathway. The ras pathway may be activated by way of ras gene mutation, elevated level of ras gene expression, elevated stability of the ras gene message, or any mutation or other mechanism which leads to the activation of ras or a factor or factors downstream or upstream from ras in the ras pathway, thereby increasing the ras pathway activity. For example, activation of EGF receptor, PDGF receptor or sos results in activation of the ras pathway. Ras-mediated neoplastic cells include, but are not limited to, ras-mediated cancer cells, which are cells proliferating in a malignant manner due to activation of the ras pathway.

"Infection by reovirus" refers to the entry and replication of reovirus in a cell. Similarly, "infection of a tumor by reovirus" refers to the entry and replication of reovirus in the cells of the tumor.

"Reovirus" refers to any virus classified in the reovirus genus, whether naturally occurring, modified or recombinant. Reoviruses are viruses with a double-stranded, segmented RNA genome. The virions measure 60–80 nm in diameter and possess two concentric capsid shells, each of which is icosahedral. The genome consists of double-stranded RNA in 10–12 discrete segments with a total genome size of 16–27 kbp. The individual RNA segments vary in size. Three distinct but related types of reovirus have been recovered from many species. All three types share a common complement-fixing antigen.

The human reovirus consists of three serotypes: type 1 (strain Lang or T1L), type 2 (strain Jones, T2J) and type 3 (strain Dearing or strain Abney, T3D). The three serotypes are easily identifiable on the basis of neutralization and hemagglutinin-inhibition assays (see, for example, Fields, B. N. et al., 1996).

The reovirus may be naturally occurring or modified. The reovirus is "naturally-occurring" when it can be isolated from a source in nature and has not been intentionally modified by humans in the laboratory. For example, the reovirus can be from a "field source", that is, from a human who has been infected with the reovirus.

The reovirus may be modified but still capable of lytically infecting a mammalian cell having an active ras pathway. The reovirus may be chemically or biochemically pretreated (e.g., by treatment with a protease, such as chymotrypsin or trypsin) prior to administration to the proliferating cells. Pretreatment with a protease removes the outer coat or capsid of the virus and may increase the infectivity of the virus. The reovirus may be coated in a liposome or micelle (Chandran and Nibert, 1998). For example, the virion may be treated with chymotrypsin in the presence of micelle forming concentrations of alkyl sulfate detergents to generate a new infectious subvirion particle.

The reovirus may be a recombinant reovirus resulting from the recombination/reassortment of genomic segments from two or more genetically distinct reoviruses. Recombination/reassortment of reovirus genomic segments may occur in nature following infection of a host organism with at least two genetically distinct reoviruses. Recombinant virions can also be generated in cell culture, for example, by co-infection of permissive host cells with genetically distinct reoviruses (Nibert et al. 1995).

Accordingly, the invention contemplates the use of a recombinant reovirus resulting from reassortment of genome segments from two or more genetically distinct reoviruses, including but not limited to, human reovirus, such as type 1 (e.g., strain Lang), type 2 (e.g., strain Jones), and type 3 (e.g., strain Dearing or strain Abney), non-human mammalian reoviruses, or avian reovirus. The invention further contemplates the use of recombinant reoviruses resulting from reassortment of genome segments from two or more genetically distinct reoviruses wherein at least one parental virus is genetically engineered, comprises one or more chemically synthesized genomic segment, has been treated with chemical or physical mutagens, or is itself the result of a recombination event. The invention further contemplates the use of the recombinant reovirus that has undergone recombination in the presence of chemical mutagens, including but not limited to dimethyl sulfate and ethidium bromide, or physical mutagens, including but not limited to ultraviolet light and other forms of radiation.

The invention further contemplates the use of recombinant reoviruses that comprise deletions or duplications in one or more genome segments, that comprise additional genetic information as a result of recombination with a host cell genome, or that comprise synthetic genes.

The reovirus may be modified by incorporation of mutated coat proteins, such as for example, into the virion outer capsid. The proteins may be mutated by replacement, insertion or deletion. Replacement includes the insertion of different amino acids in place of the native amino acids. Insertions include the insertion of additional amino acid residues into the protein at one or more locations. Deletions include deletions of one or more amino acid residues in the protein. Such mutations may be generated by methods known in the art. For example, oligonucleotide site directed mutagenesis of the gene encoding for one of the coat proteins could result in the generation of the desired mutant coat protein. Expression of the mutated protein in reovirus infected mammalian cells in vitro such as COS 1 cells will result in the incorporation of the mutated protein into the reovirus virion particle (Turner and Duncan, 1992; Duncan et al., 1991; Mah et al., 1990).

The reovirus is preferably a reovirus modified to reduce or eliminate an immune reaction to the reovirus. Such a modified reovirus is termed "immunoprotected reovirus". Such modifications could include packaging of the reovirus in a liposome, a micelle or other vehicle to mask the reovirus from the immune system. Alternatively, the outer capsid of the reovirus virion particle may be removed since the proteins present in the outer capsid are the major determinant of the host humoral and cellular responses.

"Administration" of a virus to a subject refers to the act of administering the virus to a subject in a manner so that it contacts the target neoplastic cells. The route by which the virus is administered, as well as the formulation, carrier or vehicle, will depend on the location as well as the type of the target cells. A wide variety of administration routes can be employed and is discussed below in further detail.

An "oncolytic virus" is a virus that preferentially replicates in, and kills, neoplastic cells. An oncolytic virus may be a naturally-occurring virus or an engineered virus. Oncolytic viruses also encompass immunoprotected and reassortant viruses as described in detail for reovirus. The virus is "naturally-occurring" when it can be isolated from a source in nature and has not been intentionally modified by humans in the laboratory. For example, the virus can be from a "field source", that is, from an infected animal. The virus is "engineered" when it has been modified by human intervention.

"Treating or alleviating a tumor" means alleviating or eliminating the symptoms of a tumor, or slowing down the progress of the tumor. The alleviation is preferably at least about 10%, more preferably at least about 20%, 30%, 40%, 50%, 60%, 70%, 80% or 90%.

A "metastatic tumor" is a tumor that has metastasized from a tumor located at another place in the same animal.

An "effective amount" is an amount of an irradiating agent or reovirus which is sufficient to result in the intended effect. For an irradiating agent used to treat or ameliorate a tumor, an effective amount is an amount of the irradiating agent sufficient to alleviate or eliminate the symptoms of the tumor, or to slow down the progress of the tumor. For a reovirus to sensitize a tumor to an irradiating agent, an effective amount is an amount of the reovirus sufficient to increase sensitivity of the tumor to the irradiating agent.

Methods

Reovirus is an effective therapeutic agent against ras-activated neoplasia because it selectively replicates in cells with an activated ras pathway (U.S. Pat. No. 6,136,307). The ras pathway is not activated in normal cells, therefore reovirus kills neoplastic cells with high selectivity. Without being limited to a theory, it is thought that viral gene transcription in normal cells correlated with phosphorylation of a cellular protein of approximately 65 kDa, determined to be double-stranded RNA-activated protein kinase (PKR), that was not observed in ras-activated cells. Phosphorylation of PKR leads to inhibition of translation, therefore viral replication can not be completed. In ras-activated cells, however, ras or its downstream factors blocks the phosphorylation of PKR, thereby allowing viral translation and replication to go on.

In the present invention, we unexpectedly discovered that reovirus can increase the sensitivity of neoplastic cells to radiation. A head and neck cancer patient with several lesions in the neck area had been treated with radiotherapy, but the treated lesion expanded quickly again after a moderate response. Thereafter, reovirus was injected into one of the lesions, and 50 days later a different lesion was irradiated. This time, radiation resulted in a remarkable reduction in tumor mass, indicating that reovirus can sensitize tumor cells to radiation. Moreover, these results also indicate that reovirus and radiation do not have to be administered at the same time or place, as local administration of reovirus can lead to a systemic sensitization effect (Example 1).

In the present invention, it is preferable that reovirus increases sensitivity of cells or animals to radiation by at least about 20% as compared to the effect of radiation in the absence of reovirus. The increase in sensitivity is more preferably at least about 30%, 40%, 50%, 60%, 70%, 80%, 90%, 100%, or more. In the most preferred embodiment, reovirus is useful to sensitize a tumor which is resistant to radiation in the absence of reovirus, and the sensitization effect cannot be numerically expressed.

The sensitivity of a cell or tumor to radiation can be observed or measured according to established methods in the art, which may vary with the nature of the disease. For example, sensitivity of a neoplastic cell to radiation may be determined by the size of the tumor or growth rate of the neoplastic cell (for instance see Example 1). Sensitivity may also be observed as reduction of the cognate symptoms or disease indicators, such as blood cell count in leukemia patients or liver function in hepatoma patients. Alternatively, sensitivity may be assessed as inability of the irradiated tumor to begin to expand again or to grow back to the original size. Such inability can be determined by the time it takes for the irradiated tumor to begin to expand again or to grow back to the original size after irradiation, as longer time indicates higher sensitivity to the treatment.

The present invention can be used to increase the sensitivity of neoplastic cells to any irradiating agents, including but not limited to, X-rays, gamma rays (e.g., gamma rays produced by radium, uranium, or cobalt 60), and particle beam (e.g., electrons, neutrons, pions, and heavy ions). The irradiation may be in the form of external radiotherapy or internal radiotherapy (including brachytherapy, interstitial irradiation, and intracavitary irradiation). The irradiating agents may be linked to an antibody, as in radioimmunotherapy, or employed during a surgery, as in intraoperative radiotherapy.

The reovirus is administered in a manner so that it can ultimately contact the target neoplastic cells. The route by which the reovirus is administered, as well as the formulation, carrier or vehicle, will depend on the location as well as the type of the target cells. A wide variety of administration routes can be employed. For example, for a solid neoplasm that is accessible, the reovirus can be administered by injection directly to the neoplasm. For a hematopoietic neoplasm, for example, the reovirus can be administered intravenously or intravascularly. For neoplasms that are not easily accessible within the body, such as metastases, the reovirus is administered in a manner such that it can be transported systemically through the body of the mammal and thereby reach the neoplasm (e.g., intravenously or intramuscularly). Alternatively, the reovirus can be administered directly to a single solid neoplasm, where it then is carried systemically through the body to metastases. The reovirus can also be administered subcutaneously, intraperitoneally, intrathecally (e.g., for brain tumor), topically (e.g., for melanoma), orally (e.g., for oral or esophageal neoplasm), rectally (e.g., for colorectal neoplasm), vaginally (e.g., for cervical or vaginal neoplasm), nasally or by inhalation spray (e.g., for lung neoplasm).

The reovirus or irradiating agent can be administered in a single dose, or multiple doses (i.e., more than one dose). The multiple doses can be administered concurrently at different sites or by different routes, or consecutively (e.g., over a period of days or weeks). The reovirus is preferably administered prior to or concurrently with the radiation.

The reovirus is preferably formulated in a unit dosage form, each dosage containing from about $10^2$ pfus to about $10^{13}$ pfus of the reovirus. The term "unit dosage forms" refers to physically discrete units suitable as unitary dosages for human subjects and other mammals, each unit containing a predetermined quantity of reovirus calculated to produce the desired therapeutic effect, in association with a suitable pharmaceutical excipient.

The present invention can be applied to any animal subject, preferably a mammal. The mammal is preferably selected from the group consisting of canine, feline, rodent, domestic livestock (such as sheep, goats, cattle, horses, and pigs), human and non-human primates. Preferably, the mammal is human.

It is contemplated that the present invention may be combined with other tumor therapies such as chemotherapy, surgery, and/or immunotherapy.

The present invention further provides a method of preventing a tumor in a subject from developing resistance to radiation by administering an effective amount of reovirus to the subject prior to exposing the subject to radiation. As discussed above, the reovirus can be administered in any manner that ultimately leads to contact of the tumor with reovirus, such as intravenously, intramuscularly, and subcutaneously. Preferably, the reovirus is administered into the target tumor.

In addition to reovirus, other oncolytic viruses can be used to practice the present invention in the same manner as reovirus. In particular, the oncolytic virus can be administered to a different site or at a different time as the radiation. For example, the virus can be administered systemically and the radiation is given to one local tumor. As a result, the local tumor that is irradiated shows higher sensitivity to radiation than in the absence of the virus. Moreover, other tumors in the same subject, which have not received the virus or irradiation, can also become more sensitive to radiation than in the absence of the virus. Similarly, the virus may be administered to a local tumor while another local tumor is irradiated, and both these tumors, as well as other tumors in the same animal, can be more effectively treated with radiation than in the absence of the virus.

A few oncolytic viruses are discussed below, and a person of ordinary skill in the art can practice the present invention using additional oncolytic viruses as well according to the disclosure herein and knowledge available in the art. The oncolytic virus may be a member in the family of myoviridae, siphoviridae, podpviridae, teciviridae, corticoviridae, plasmaviridae, lipothrixviridae, fuselloviridae, poxyiridae, iridoviridae, phycodnaviridae, baculoviridae, herpesviridae, adnoviridae, papovaviridae, polydnaviridae, inoviridae, microviridae, geminiviridae, circoviridae, parvoviridae, hepadnaviridae, retroviridae, cyctoviridae, reoviridae, birnaviridae, paramyxoviridae, rhabdoviridae, filoviridae, orthomyxoviridae, bunyaviridae, arenaviridae, leviviridae, picornaviridae, sequiviridae, comoviridae, potyviridae, caliciviridae, astroviridae, nodaviridae, tetraviridae, tombusviridae, coronaviridae, glaviviridae, togaviridae, or barnaviridae. As with reovirus, immunoprotected or reassortant viruses of other oncolytic viruses are also encompassed in the present invention. Furthermore, a combination of at least two oncolytic viruses, including reovirus, can also be employed to practice the present invention.

Normally, when virus enters a cell, double stranded RNA Kinase (PKR) is activated and blocks protein synthesis, and the virus can not replicate in this cell. Some viruses have developed a system to inhibit PKR and facilitate viral protein synthesis as well as viral replication. For example, adenovirus makes a large amount of a small RNA, VA1 RNA. VA1 RNA has extensive secondary structures and binds to PKR in competition with the double stranded RNA (dsRNA) which normally activates PKR. Since it requires a minimum length of dsRNA to activate PKR, VA1 RNA does not activate PKR. Instead, it sequesters PKR by virtue of its large amount. Consequently, protein synthesis is not blocked and adenovirus can replicate in the cell.

Ras-activated neoplastic cells are not subject to protein synthesis inhibition by PKR, because ras inactivates PKR. These cells are therefore susceptible to viral infection even if the virus does not have a PKR inhibitory system. Accordingly, if the PKR inhibitors in adenovirus, vaccinia virus, herpex simplex virus or parapoxvirus orf virus is mutated so as not to block PKR function anymore, the resulting viruses do not infect normal cells due to protein synthesis inhibition by PKR, but they replicate in ras-activated neoplastic cells which lack PKR activities.

Accordingly, a virus that is modified or mutated such that it does not inhibit PKR function selectively replicates in ras-activated neoplastic cells while normal cells are resistant. Preferably, the virus is an adenovirus mutated in the VA1 region, a vaccinia virus mutated in the K3L and/or E3L region, a parapoxvirus orf virus mutated in the OV20.0L gene, or an influenza virus mutated in the NS-1 gene. The virus is preferably not a herpes virus mutated in the $\gamma_1 34.5$ gene.

The viruses can be modified or mutated according to the known structure-function relationship of the viral PKR inhibitors. For example, since the amino terminal region of E3 protein interacts with the carboxy-terminal region domain of PKR, deletion or point mutation of this domain prevents anti-PKR function (Chang et al., 1992, 1993, 1995; Sharp et al., 1998; Romano et al., 1998). The K3L gene of vaccinia virus encodes pK3, a pseudosubstrate of PKR. There is a loss-of-function mutation within K3L. Truncations or point mutations within the C-terminal portion of K3L protein that is homologous to residues 79 to 83 in eIF-2 abolish PKR inhibitory activity (Kawagishi-Kobayashi et al., 1997).

Another example is the Delta24 virus which is a mutant adenovirus carrying a 24 base pair deletion in the E1A region (Fueyo et al., 2000). This region is responsible for binding to the cellular tumor suppressor Rb and inhibiting Rb function, thereby allowing the cellular proliferative machinery, and hence virus replication, to proceed in an uncontrolled fashion. Delta24 has a deletion in the Rb binding region and does not bind to Rb. Therefore, replication of the mutant virus is inhibited by Rb in a normal cell. However, if Rb is inactivated and the cell becomes neoplastic, Delta24 is no longer inhibited. Instead, the mutant virus replicates efficiently and lyses the Rb-deficient cell.

In addition, vesicular stomatitis virus (VSV) selectively kills neoplastic cells (and interferon can be optionally added). A herpes simplex virus 1 (HSV-1) mutant which is defective in ribonucleotide reductase expression, hrR3, was shown to replicate in colon carcinoma cells but not normal liver cells (Yoon et al., 2000). Newcastle disease virus (NDV) replicates preferentially in malignant cells, and the most commonly used strain is 73-T (Reichard et al., 1992; Zorn et al, 1994; Bar-Eli et al, 1996). Vaccinia virus propagated in several malignant tumor cell lines. Encephalitis virus was shown to have an oncolytic effect in a mouse sarcoma tumor, but attenuation may be required to reduce its infectivity in normal cells. Tumor regression have been described in tumor patients infected with herpes zoster, hepatitis virus, influenza, varicella, and measles virus (for a review, see Nemunaitis, 1999).

The oncolytic virus may be naturally occurring or modified. The virus may be chemically or biochemically pretreated (e.g., by treatment with a protease, such as chymotrypsin or trypsin) prior to administration to the neoplastic cells. Pretreatment with a protease removes the outer coat or capsid of the virus and may increase the infectivity of the virus. The virus may be coated in a liposome or micelle (Chandron and Nibert, 1998) to reduce or prevent an immune response from a mammal which has developed immunity to the virus. For example, the virion may be treated with chymotrypsin in the presence of micelle forming concentrations of alkyl sulfate detergents to generate a new infectious subvirion particle. The oncolytic virus may also be a reassortant virus.

It is preferable that the virus is not a vehicle for delivering a gene for the purpose of gene therapy. For example, viruses have been engineered to deliver the adenoviral E1A gene, the p53 tumor suppressor gene, prodrug-encoding genes (Chmura et al., 1999; 2001) or genes under a radiation-inducible promoter. These viruses, in fact, usually do not replicate preferentially in neoplastic cells and are hence not oncolytic viruses. It is also preferable that the virus is not an engineered adenovirus or herpes virus, or a virus that expresses a functional E1A protein.

When the virus is administered systemically to immunocompetent mammals, the mammals may produce an immune response to the virus. Such an immune response may be avoided if the virus is of a subtype to which the mammal has not developed immunity, or the virus has been modified as previously described herein such that it is immunoprotected, for example, by protease digestion of the outer capsid or packaging in a micelle.

Alternatively, it is contemplated that the immunocompetency of the mammal against the virus may be suppressed either by the co-administration of pharmaceuticals known in the art to suppress the immune system in general (Cuff et al., 1998) or alternatively by administration of anti-antivirus antibodies. The humoral immunity of the mammal against virus may also be temporarily reduced or suppressed by plasmaphoresis of the blood to remove anti-virus antibodies. The humoral immunity of the mammal against virus may additionally be temporarily reduced or suppressed by intravenous administration of non-specific immunoglobulin to the mammal.

It is contemplated that the virus may be administered to immunocompetent mammals in conjunction with the administration of anti-antivirus antibodies. Anti-antivirus antibodies used in this invention are selected, for example, from anti-antireovirus antibodies, anti-antiadenovirus antibodies, anti-antiHSV antibodies, anti-antivaccinia virus antibodies, anti-antiinfluenza antibodies and anti-antiparapoxvirus orf virus antibodies. Such antibodies can be made by methods known in the art (see, for example, Harlow et al.,1988). Such anti-antivirus antibodies may be administered prior to, at the same time or shortly after the administration of the virus. Preferably an effective amount of the anti-antivirus antibodies are administered in sufficient time to reduce or eliminate an immune response by the mammal to the virus.

In one embodiment of this invention a course of virus therapy is administered one or more times. Following the first administration of virus therapy particular immune constituents that may interfere with subsequent administrations of the virus are removed from the patient. These immune constituents include B cells, T cells, antibodies, and the like.

Removal of either the B cell or T cell population can be accomplished by several methods. In one method, the blood may be filtered and heme-dialysis may be performed. Another method is the filtration of the blood coupled with extra corporeal compounds that can remove the cell populations, for example, with immobilized antibodies that recognize specific receptors on the cell population which is to be removed. Yet another method for removal of a cell population is by immune suppression. This can be done by first line radiation therapy or by cyclic steroids such as cyclosporin.

Selective removal of anti-virus antibodies can also prevent the patient's immune system from removing therapeutically administered virus. Antibodies can be removed by several methods, including heme-dialysis and passing the blood over immobilized virus (selective antibody removal); by removal of all IgG antibodies by heme-dialysis and passing the blood over immobilized protein A (commercially available as PROSORBA, Cypress Bioscience, San Diego, Calif.); or by administration of humanized anti-idiotypic antibodies, where the idiotype is against the virus to be administered.

Another method of this invention is to allow virus to act systemically without impairing normal immune function by masking or impairing immune recognition of virus. To prevent the patient's immune system from recognizing the administered virus, the virus may be coated with non-virotoxic humanized antibodies, such as coating with the $F_{ab}$ portion of the antibody, or coated in a micelle. Additionally, the virus may be treated with chymotrypsin to yield an infectious subviral particle (ISVP). An ISVP may be used either alone or in combination with whole virus to provide an agent that is either poorly recognized or has not been previously prevented by the patient's immune system.

Another embodiment of this invention includes the removal of virus from the patient following administration. Since this method may be used on patients that are either immune suppressed or immune incompetent, it may be of importance to remove virus from the blood stream following the course of treatment. The virus may be removed by affinity chromatography using extra corporeal anti-virus antibodies associated with heme dialysis, B-cell proliferative agents, or adjuvants to stimulate immune response against the virus, such as UV inactivated virus or Freund's adjuvant.

The following examples are offered to illustrate this invention and are not to be construed in any way as limiting the scope of the present invention.

EXAMPLES

In the examples below, the following abbreviations have the following meanings. Abbreviations not defined have their generally accepted meanings.

| | |
|---|---|
| OC= | degree Celsius |
| hr= | hour |
| min= | minute |
| μM= | micromolar |
| mM= | millimolar |
| M= | molar |
| ml= | milliliter |
| μl= | microliter |
| mg= | milligram |
| μg= | microgram |
| FBS= | fetal bovine serum |
| DTT= | dithiothrietol |
| PBS= | phosphate buffered saline |
| DMEM= | Dulbecco's modified Eagle's medium |
| MEM= | modified Eagle's medium |
| MOI= | multiplicity of infection |
| PFU= | plaque forming units |
| PKR= | double-stranded RNA activated protein kinase |
| EGF= | epidermal growth factor |
| PDGF= | platelet derived growth factor |
| DMSO= | dimethylsulfoxide |
| CPE= | cytopathic effect |
| cGy= | centiGray |

Example 1

Combination of Reovirus and Radiation Therapies

A 48 year old female patient had head and neck tumor (nasopharyngeal). There were three large lesions in the neck area, one on the right side, one under the jaw, and the third one on the left side. The one on the right side was the largest and covered almost from her ear to her shoulder. The patient had been treated with chemotherapy and radiation therapy with either no effect or recurrence shortly after a moderate response.

After chemotherapy and radiation therapy, the patient was treated with reovirus therapy. Thus, $1\times10^9$ Dearing strain reovirus was injected into the left side lesion on Days 0, 2 and 4, respectively. The reovirus was prepared as previously described (U.S. Patent Application Publication No. 20020037576). The tumors were measured on Day 0 as the baseline level for each tumor. As shown in Table 1, the left side lesion and the lesion under the jaw measured about 4 $cm^2$ and 19 $cm^2$ on Day 0, respectively. The right side lesion was not measured as it was too large to be measured meaningfully.

TABLE 1

Tumor size, serum PTPCR and antibody titer after reovirus administration

| | Tumor Size Measurements | | Serum | |
|---|---|---|---|---|
| | Lesion on the left side | Lesion under the jaw | Reovirus by RTPCR | Serum Antibody Titer |
| Day 0 | 4.39 | 18.87 | negative | <8 |
| Day 7 | 4.56 | 13.95 | negative | 1024 |
| Day 14 | 6.76 | 18.62 | negative | 1024 |
| Day 21 | 7 | 31.5 | negative | 1024 |
| Day 28 | 4.08 | 28.06 | negative | 1024 |
| Day 35 | 4.14 | 17.1 | negative | 1024 |
| Day 42 | 4.83 | 19.6 | positive | 1024 |
| Day 70 | 1.12 | 21.12 | negative | 1024 |
| Day 98 | 4 | 4.64 | negative | 1024 |

For other baseline measurements, blood was obtained from the patient to determine the presence of reovirus by reverse transcription polymerase chain reaction (RTPCR) using reovirus specific primers. In addition, the titer of anti-reovirus neutralizing antibodies in the patient serum was determined as well, which was performed by incubating diluted serum samples with a culture of L929 cells and reovirus. Whereas infection of L929 cells by reovirus results in cytopathic effect (CPE) in the infected cells, CPE can be inhibited by anti-reovirus neutralizing antibodies. Thus, the presence of neutralizing antibodies in the serum is indicated by inhibition of CPE in this assay, and the highest dilution factor of serum that was capable of inhibiting 50% of the cells from developing CPE was deemed titer of the antibodies. As shown in Table 1, reovirus could not be detected by RTPCR on Day 0, and the level of anti-reovirus neutralizing antibodies was negligibly low.

Tumor size, reovirus and anti-reovirus antibodies were then measured periodically and the results are shown in Table 1. Both the left side tumor and the lesion under the jaw continued to enlarge for a few weeks. However, on Day 28, tumor measurements revealed that the lesion on the left side (the injected site) decreased in size and was palpably softer. The lesion under the jaw was also reduced slightly. The lesion on the right side was too large to be measured accurately, but it appeared unchanged. Significant levels of anti-reovirus antibodies appeared in the serum after reovirus injection, indicating that reovirus replicated in the patient and was recognized by the immune system. Occasionally, viral particles could even be detected in the blood by RT-PCR. Therefore, reovirus had spread beyond the injection site.

On Day 50, the patient received radiation therapy to the right side tumor mass only using electron beams, at a tumor dose of 3000 cGy defined at 100% isodose in ten daily fractions for 14 days. Surprisingly, visual assessment on Day 70 revealed that this tumor showed some shrinkage even though the irradiation had been initiated for only 20 days. By Day 98, this tumor was reduced to about 10–25% of the baseline size. Thus, reovirus is capable of sensitizing tumor cells to radiation therapy. This effect is not limited to the cells that have been contacted directly with reovirus, as the cells in the right side tumor mass were not injected with reovirus. This phenomenon is consistent with our previous observation that treating one tumor in a subject with reovirus can lead to reduction of another tumor in the same subject.

Furthermore, the lesion on the left side, which was injected with reovirus but not irradiated, shrank to a quarter of the baseline size 20 days after irradiation of the right side lesion (Day 70), indicating that radiation and reovirus administration may induce a bystander effect on each other. As another putative result of the bystander effect, the lesion under the jaw, which was neither in the radiation field nor injected with reovirus, shrank to a quarter of the baseline size on Day 98.

In view of these results, the combination of reovirus therapy and radiation therapy is a surprisingly effective treatment regime, and its effect is not limited to the lesions that receive either reovirus or radiation. Instead, all tumors in the same subject, including metastatic tumors, are inhibited by the combination of reovirus and radiation.

We claim:

1. A method of sensitizing a ras-activated neoplastic cell to irradiation, wherein the neoplastic cell is resistant to an irradiating agent in the absence of reovirus, comprising:
   (a) determining whether the neoplastic cell is resistant to an irradiating agent in the absence of reovirus, wherein the determination indicates that the neoplastic cell is resistant to the irradiating agent in the absence of reovirus;
   (b) administering to said neoplastic cell an effective amount of a reovirus under conditions that result in infection of the cells by the reovirus; and
   (c) then subjecting said cell to an effective dose of the irradiating agent, whereby the sensitivity of the neoplastic cell to the irradiating agent is increased by the reovirus.

2. The method of claim 1 wherein the neoplastic cell is located in a mammal.

3. The method of claim 2 wherein the mammal is selected from the group consisting of dogs, cats, rodents, sheep, goats, cattle, horses, pigs, human and non-human primates.

4. The method of claim 1 wherein the irradiating agent is selected from the group consisting of electrons, X-ray and gamma ray.

5. The method of claim 1 wherein the irradiating agent is gamma ray.

6. The method of claim 1 wherein the reovirus is a mammalian reovirus.

7. The method of claim 6 wherein the mammalian reovirus is a human reovirus.

8. The method of claim 7 wherein the human reovirus is a serotype 3 reovirus.

9. The method of claim 8 wherein the serotype 3 reovirus is a Dearing strain reovirus.

10. The method of claim 1 wherein the reovirus is a recombinant reovirus.

11. A method of treating or ameliorating a tumor comprising ras-activated cells in a subject, comprising:
    (a) determining whether the tumor is resistant to an irradiating agent in the absence of reovirus, wherein the determination indicates that the tumor is resistant to the irradiating agent in the absence of reovirus;
    (b) administering to the subject an effective amount of reovirus under conditions that result in infection of cells of the tumor by the reovirus; and
    (c) then irradiating the subject with an effective dose of an irradiating agent while maintaining the subject's immunocompetence,
    wherein the irradiating agent and the reovirus are administered to different sites.

12. The method of claim 11 wherein the reovirus is administered in multiple doses.

13. The method of claim 11 wherein the subject is a mammal.

14. The method of claim 11 wherein the mammal is selected from the group consisting of dogs, cats, rodents, sheep, goats, cattle, horses, pigs, humans and non-human primates.

15. The method of claim 11 wherein the tumor is a solid tumor.

16. The method of claim 15 wherein the solid tumor is selected from the group consisting of lung cancer, prostate cancer, colorectal cancer, thyroid cancer, renal cancer, adrenal cancer, liver cancer, pancreatic cancer, breast cancer and central and peripheral nervous system cancer.

17. The method of claim 16 wherein the reovirus is administered into or near the solid tumor.

18. The method of claim 11 wherein the reovirus is administered systematically.

19. The method of claim 11 wherein the tumor is a hematopoietic tumor.

20. The method of claim 19 wherein the hematopoietic tumor is selected from the group consisting of lymphomas and leukemias.

21. The method of claim 11 wherein the tumor is a metastatic tumor.

22. The method of claim 11 wherein the reovirus is a recombinant reovirus.

23. A method of treating or ameliorating a tumor comprising ras-activated cells in a subject, comprising:
(a) determining whether the tumor is resistant to an irradiating agent in the absence of reovirus, wherein the determination indicates that the tumor is resistant to the irradiating agent in the absence of reovirus;
(b) administering to the subject an effective amount of a reovirus under conditions that result in infection of cells of the tumor by the reovirus; and
(c) then irradiating the subject with an effective dose of an irradiating agent.

24. A method of treating or ameliorating a tumor comprising ras-activated cells in a subject, comprising:
(a) determining whether the tumor is resistant to an irradiating agent in the absence of reovirus, wherein the determination indicates that the tumor is resistant to the irradiating agent in the absence of reovirus;
(b) administering to the subject an effective amount of a reovirus under conditions that result in infection of cells of the tumor by the reovirus; and
(c) then irradiating the subject with an effective dose of an irradiating agent while maintaining the subject's immunocompetence,
whereby the sensitivity of the tumor to the irradiating agent is increased by the reovirus.

25. A method of treating or ameliorating a tumor comprising ras-activated cells in a subject, comprising:
(a) determining whether the tumor is resistant to an irradiating agent in the absence of reovirus, wherein the determination indicates that the tumor is resistant to the irradiating agent in the absence of reovirus;
(b) administering to the subject an effective amount of a reovirus under conditions that result in infection of cells of the tumor by the reovirus; and
(c) then irradiating the subject with an effective dose of an irradiating agent,
wherein the irradiating agent and the reovirus are administered to different sites.

* * * * *